United States Patent [19]
Weissman et al.

[11] Patent Number: 5,861,246
[45] Date of Patent: Jan. 19, 1999

[54] MULTIPLE SELECTION PROCESS FOR BINDING SITES OF DNA-BINDING PROTEINS

[75] Inventors: Sherman M. Weissman; Girish N. Nallur, both of New Haven, Conn.; Prakash Kulkarni, Columbia, Md.

[73] Assignee: Yale University, New Haven, Conn.

[21] Appl. No.: 590,571

[22] Filed: Jan. 24, 1996

[51] Int. Cl.$^6$ ............... C12Q 1/68; C07H 21/04; C12P 19/34
[52] U.S. Cl. ............... 435/6; 435/7.1; 435/91.1; 435/91.2; 536/24.1
[58] Field of Search ............... 435/6, 7.1, 91.1, 435/91.2; 536/24.1

[56] References Cited

FOREIGN PATENT DOCUMENTS

WO 94/21825  9/1994  WIPO .
WO 94/27719  12/1994  WIPO .

OTHER PUBLICATIONS

Blackwell and Weintraub, "Differences and Similarities in DNA–Binding Preferences of MyoD and E2A Protein Complexes Revealed by Binding Site Selection," *Science 250:* 1104–1110, 1990.

Blackwell et al., "Sequence–Specific DNA Binding by the c–Myc Protein," *Science 250:* 1149–1151, 1990.

Chittenden et al., "The T/E1A–Binding Domain of the Retinoblastoma Product Can Interact Selectively with a Sequence–Specific DNA–Binding Protein," *Cell* 65:1073–1082, 1991.

Ellington and Szostak, "In vitro selection of RNA molecules that bind specific ligands," *Nature 346:* 818–822, 1990.

Funk and Wright, "Cyclic amplification and selection of targets for multicomponent complexes: Myogenin interacts with factors recognizing binding sites for basic helix–loop helix, nuclear factor 1, myocyte–specific enhancer–binding factor 2, and COMP1 factor," *Proc. Natl. Acad. USA* 89:9484–9488, 1992.

Henrissat et al., "Cellulase families revealed by hydorphobic cluster analysis," *Gene 81:*83–95, 1989.

Kinzler and Vogelstein, "Whole genome PCR: application to the identification of sequence bound by gene regulatory proteins," *Nucleic Acids Research* 17(10):3645–3653, 1989.

Mavrothalassitis et al., "Laboratory Methods. Defining Target Sequences ofr DNA–Binding Proteins by Random Selection and PCR: Determination of the GCN4 Binding Sequence Repertoire," *DNA and Cell Biology* 9(10):783–788, 1990.

Pollock and Treisman, "A sensitive method for the determination of protein–DNA binding specificities," *Nucleic Acids Research* 18(21):6197–6204, 1990.

Thiessen and Bach, "Target Detection Assay (TDA): a versatile procedure to determine DNA binding sites as demonstrated on SP1 protein," *Nucleic Acids Research* 18(11): 3203–3209, 1990.

Tuerk and Gold, "Systematic Evolution of Ligands by Exponential Enrichment: RNA Ligands to Bacteriophage T4 DNA Polymerase," *Science 249:*505–510, 1990.

Wright and Funk, "CASTing for multicomponent DNA–binding complexes," *Trends in Biochemical Sciences* 18:77–80, 1993.

Wright et al., "Cyclic amplification and selection of targets (CASTing) for myogenin consensus binding site", Mol. Cell. Biol. 11:4104–4110, Aug. 1991.

Pierrou et al., "Selection of High–Affinity Binding Sites for Sequence–Specific, DNA Binding Proteins from Random Sequence Oligonucleotides," *Analytical Biochemistry* 229:99–105, 1995.

Rudert and Trucco, "DNA polymers of protein binding sequences generated by PCR," *Nucleic Acids Research* 18(21):6460, 1990.

*Primary Examiner*—Jasemine C. Chambers
*Assistant Examiner*—Scott D. Priebe
*Attorney, Agent, or Firm*—Seed and Berry LLP

[57] ABSTRACT

Methods are provided for isolating binding sites of DNA-binding proteins. An extract, such as a nuclear extract, containing DNA-binding proteins is mixed with oligonucleotide duplexes comprising a random sequence. Bound duplexes are isolated and amplified. Methods are also provided for identifying DNA-binding proteins using isolated binding sites.

10 Claims, 5 Drawing Sheets

MULTIPLE SELECTION PROCESS FOR BINDING SITES OF DNA-BINDING PROTEINS

STATEMENT OF GOVERNMENT INTEREST

Partial funding of the research that led to the making of this invention was provided by the United States Government. Accordingly, the United States Government may have certain statutory rights to this invention under 35 USC 200 et seq.

BACKGROUND OF THE INVENTION

In eucaryotic species, protein synthesis is accomplished by a dual-step process in which the cell's genetic sequence is first transcribed into a messenger RNA sequence, which in turn is translated into a specific peptide. The first step of this process, wherein RNA is synthesized on a DNA template, is known as transcription, and results in the synthesis of the mRNAs that carry the information for protein synthesis, as well as the transfer, ribosomal and other RNA molecules that have structural and catalytic functions within the cell. These RNA molecules are synthesized by one or more enzymes, RNA polymerases, which make RNA copies of the DNA sequence. However, before this synthesis can begin, the free RNA polymerase molecules must come into contact and bind with very specific DNA sequences, called the promoter, that contains the start site for RNA synthesis and signals where RNA synthesis should begin.

Although the process of transcription is similar in eucaryotes and procaryotes, the process is more complex in eucaryotic species. For example, whereas the procaryotic RNA polymerases can bind directly to their promoter, the eucaryotic enzymes can bind to their promoters only in the presence of additional protein factors already on the DNA. Thus, one or more sequence-specific DNA-binding proteins must be bound to the DNA to form a functional promoter. These protein factors are called transcription factors and are necessary for the initiation of RNA synthesis.

The proliferation and differentiation of eucaryotic cells is a complex phenomena initiated by a vast number of extracellular signals. These may include, for example, various soluble factors such as pharmaceuticals, toxins or extracellular and intracellular byproducts; matrix proteins; and adhesion molecules. These signals are passed intracellularly through a variety of signal transduction processes and lead to the activation of a set of early response genes, some of which encode transcription factors thereby leading to the initiation of a cascade of gene-protein interactions and ultimately to long-term alterations in gene expression.

The importance of transcription factor cascades in cell proliferation and differentiation is a major focus of study in modern biology. For instance, studies of transcriptional control mechanisms underlying spatially restricted transcription in the early embryonic development of Drosophila [see A. Kane, *Development* 101:1 (1987)], lineage specification in muscle [see B. Buckingham, *Curr. Opin. in Genetics and Dev.* 4:745 (1994)] and nerve cells [see Lee et. al., *Science* 268:836 (1995)], in mammary cell differentiation [see Despraz et al., *Mol. Cell Biol.* 15:3398 (1995)], and many other examples illustrate that gene protein interactions initiated by key transcription factors bring about long term changes in gene expression. These changes often involve the activation of other transcription factors which control downstream processes. Cellular differentiation and proliferation can, therefore, be regarded as an integrated process involving the concerted and sequential action of transcription factors that determine the specific biology of the cell type.

A typical cell in humans expresses about 10,000 genes. By extrapolation from lower organisms, about 2–20% of these genes are believed to encode transcription factors. Each cell type could, therefore, express as many as 200–2000 different transcription factors. Identifying transcription factors has been a time-consuming and tedious task that often requires large amounts of biological material, or depends upon the availability of mutants, and in general, has yielded one new factor per investigation. There is a need, therefore, to provide alternative means to identify and study the transcription factors per se, as well as allow investigation into their biological function.

To overcome the problems with conventional methods, a direct approach is provided herein for the comprehensive isolation of binding sites recognized by a large cross-section of the transcription factors present in any cell type based upon their property to bind DNA in a sequence-specific manner. The potential applications of this approach in preparing cell type specific binding site sub-libraries is also described in this specification.

In present invention, a number of sequence-specific DNA binding properties of transcription factors were exploited in an approach to obtain the direct isolation of binding sites recognized by a large number of protein factors. These binding sites serve as efficient probes for isolation of the cognate factors. The approach is rapid, and can be reiterated to derive progressively more information from the products of each study.

SUMMARY OF THE INVENTION

It is, therefore, an aspect of the present invention is an integrated approach to identify a majority of proteins present in a cell type, using Jurkat T-cells as the best embodiment of a universal working-example of the present invention, that bind to DNA in a sequence specific manner.

Another aspect of the present invention is the construction of a binding site library from synchronized Jurkat T-cells that have been treated with phorbol myristyl acetate (PMA) and phytohaemagglutinin (PHA).

In the protocol according to the present invention, a library of binding sites was first constructed by repeated selection of a random pool of oligonucleotides using an electrophoretic mobility shift assay (EMSA) with nuclear extracts. The selection was conducted under conditions that favor selection of preferred binding sites. Activated Jurkat cells were used because of the extensive knowledge that has developed about this cell type (Jurkat T-cells grow rapidly in culture, can be synchronized by serum starvation, and can be stimulated to produce interleukin-2, an event in the differentiation of peripheral blood T-cells in vivo). As a result, they have become a recognized model system for the comprehensive identification and cloning of all DNA sites that are specifically recognized by protein factors present in these cells; the use of Jurkat T-cells as a model is well accepted, and the findings using this test system may readily be extrapolated to other test systems using other cell types. Thus, Jurkat cells were selected as a model system for identification and cloning of DNA sites that are specifically recognized by protein factors. Library probes were used for isolation of 'optimal' sites for cloning specific transcription factors, and for probing qualitative differences in transcription factor expression between T cells in two different physiological states.

A more thorough and complete understanding of these and other aspects of the present invention may be had by reference to the following figures, examples and detailed description of the present invention. However, it is to be understood that the following examples are provided only for their general content and are not to be taken as limitations of the scope of present invention as defined in this description or the appended claims.

Throughout the following description of the present invention, terminology specific to the technology field will be used. In order to avoid any misunderstandings as to what is being referenced, and to provide the reader with a clear understanding of what is being described, the following definitions will be used.

With regard to the use of genomic sequences used throughout this description, the oligonucleotide base sequences are depicted according to their recognized abbreviations, that is, "A" refers to adenine, "C" refers to cytosine, "G" refers to guanine, "T" refers to thymine, "M" refers to either A or C, "R" refers to either A or G, "W" refers to either A or T, "S" refers to either C or G, "Y" refers to either C or T, "K" refers to either G or T, "V" refers to either A or C or G, "H" refers to either A or C or T, "D" refers to either A or G or T, "B" refers to either C or G or T, and "N" refers to either A or C or T or G or unknown.

"HA Nuclear Extract" refers to nuclear extracts that are prepared by lysing Jurkat cells, or those from another cell line, with a hypotonic salt solution; centrifuging the lysed cells to obtain a pellet; extracting the pellet with a high salt concentration to obtain a nuclear extract; and subsequently placing this extract on a heparin agarose gel from which the HA nuclear extract is eluted.

"Heel" refers to the sequences at the 5' and 3' ends of the oligonucleotide, such that these sequences are usually not part of the binding site for the protein; the heel sequences are chosen such that primers complementary to them can be used to amplify the oligonucleotide, including the internal random sequences.

"Jurkat cells" refer to the human T-cell line Jurkat.

"T-cell" refers to lymphocytes which develop in the thymus and are responsible for cell-mediated immunity.

DETAILED DESCRIPTION OF THE INVENTION

Figure 1:
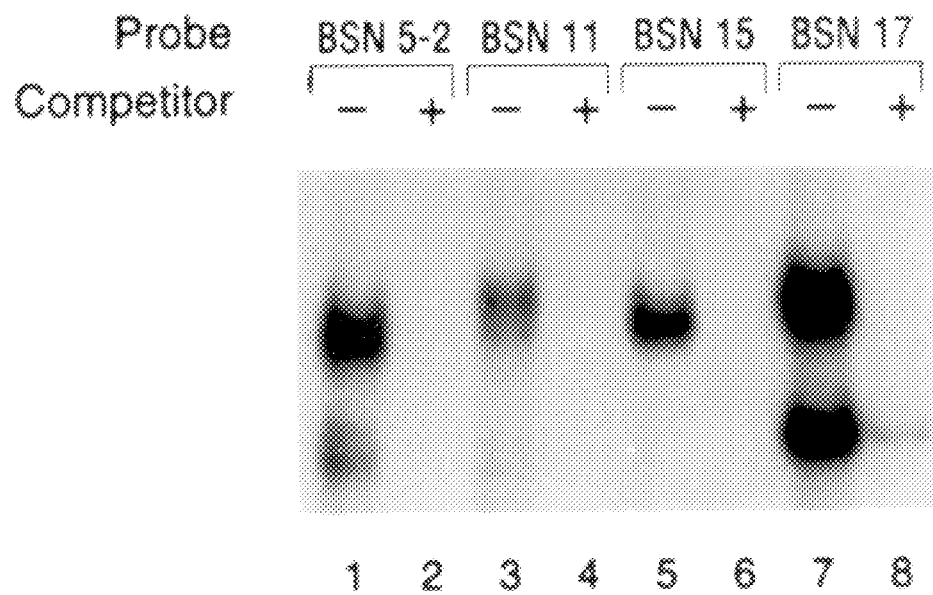
FIG. 1 depicts the EMSA analysis of randomly picked clones.

As several independent DNA-protein interactions occur simultaneously in this approach, as will be further described, the protocol of the invention is called the Multiplex Selection Technique, or MuST. The outline of the MuST protocol is fairly straight-forward, and may be generally described as having four separate steps:

(1) prepare a set of synthetic oligonucleotides ('probes') containing internal random sequences of sufficient length to contain a large number of binding sites, and a binding protein mixture consisting of a crude cell or nuclear extracts or preferably, extracts slightly purified (as with a heparin agarose column) but still sufficiently complex to contain a number of different DNA binding proteins (i.e., 'target proteins');

(2) bind probes to targets under 'optimum conditions' such that suboptimal probes are bound to a substantially lower extent than optimal probes; binding being performed in the presence of a large excess of non-specific inhibitor such as, in the specific embodiment described herein, poly dI-dC; and separate the bound from unbound probes (in the specific embodiment described herein, this separation id accomplished by taking advantage of the fact that the targets are all of much higher molecular weight than the probes, and therefore the probe-target complex will move more slowly during gel electrophoresis than will the free probes);

(3) recover the complexed probes and amplify them by PCR; use this amplified mixture as probes and repeat the binding and separation (as in step 2) to recycle the procedure a limited number of times (as for example 4x in the following description); and (4) analyze the final amplified mixture which will consist largely or entirely of specific probes.

In the above scheme, analysis can be can be done by sequencing the mixture one at a time (made more efficient by multimerizing the oligonucleotides so that one sequencing run represents several probes). Alternatively, the probes can be subdivided based on the mobility of the probe target complexes on a gel (or by some other means such as binding to an extract from a different type of cell) prior to analysis.

In the most general terms, these four steps of the MuST protocol according to the present invention may be outlined as having the following expanded flow sequence:

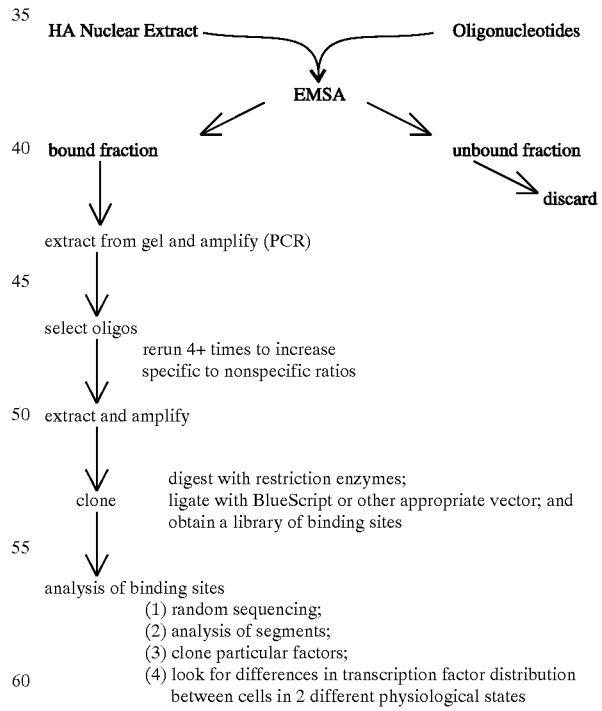

As defined in the above sequence, "oligonucleotides" admixed with the HA Nuclear Extract are randomized, i.e., oligonucleotides that contain an internal sequence in which ten successive residues are each "randomized" so that they have an independent equal probability of having any of the four bases. The number of random residues could, in principle, range from about 6 up to about 25. Beyond that point, the amount of material necessary to get representation of all sequences becomes impractically large; below 6 residues one would be examining too small a number of oligonucleotides to efficiently get information. For the embodiments described herein, ten residues were chosen, as this would be large enough to represent a significant fraction of binding sites, without being so large that it would produce complications due to higher avidity for sequences that contain two separate binding sites.

The technical beauty of the MuST procedure is essentially that by using a complex mixture of targets in the selection steps one can, in a relatively small number of selection cycles, obtain a mixture that is predominantly made up of specific probes containing optimal sequences. By starting with two complex mixtures (i.e., both probes and targets), one can obtain a high ratio of specifically retained material to non-specific background in the early cycles, without working with concentrations of probe or target such that large amounts of more weakly binding material is retained.

and sequenced. Synthetic probes representing the consensus sequences, BSO8 and BSO3/9, were used in EMSA experiments with the HA-TP2 extract and for reciprocal competitions with the wt-Oct probe (SEQ ID No. 1). Competitor oligonucleotides were: a=wt-Oct; b=BSO8. A single complex obtained in an EMSA experiment using bacterial produced Oct2 protein and TP2–4 probes is marked by an arrowhead in lane 10.

For a more complete understanding, the following is a comparison of the BSO8 and BSO3/9 consequence sequences with the HLA class II DRA promoter sequence shown in the bottom strand. In the promoter sequence, the Y-box sequence is AATCAG (Seq. ID No. 2); the X-box sequence is CTAG (Seq. ID No. 3); and the consensus wt-Oct sequence is ATGCAAAT (Seq. ID No. 4). The number of intervening nucleotides between these boxes are shown in parentheses.

|  | BSO8 |  | BSO3/9 | Seq. ID Nos. |
|---|---|---|---|---|
| Consensus | AAT_AGAA |  | CTAG | 5  3 |
| DRA Promoter | ATGCAAAT(N)$_{16}$AATCAGAA(N)$_{26}$CTAGGGGGGG |  |  | 6 |

As will be discussed in greater detail below, the Octamer binding site (ATGCAAAT; Seq. ID No. 1) was used as one embodiment of the analysis of binding sites by cloning particular factors. The embodiment to analyze differences in transcription factors distribution between cells utilized resting Jurkat cells and Jurkat cells that had been activated (or stimulated) by treatment with phorbol 12-myristate 13-acetate (PMA) or phytohemagglutinin (PHA) as outlined in Example 1.

Using this general protocol upon "resting" and "activated" cells, the present invention allows one to utilize a nuclear extract containing all transcription factor proteins to determine first the binding sites of the transcription factors (including the optimum binding sites), and then subsequently determine the transcription factors for those binding sites.

More specifically, with regard to the above figures, in the EMSA analysis shown in FIG. 1, which will be described in detail below, synthetic oligonucleotides for seven of the randomly picked clones depicted in Table I were used as probes for EMSA with the HA-TP2 (activated Jurkat cells) nuclear extract. Those that exhibited positive EMSA shifts are shown in the figure.

Figure 2:
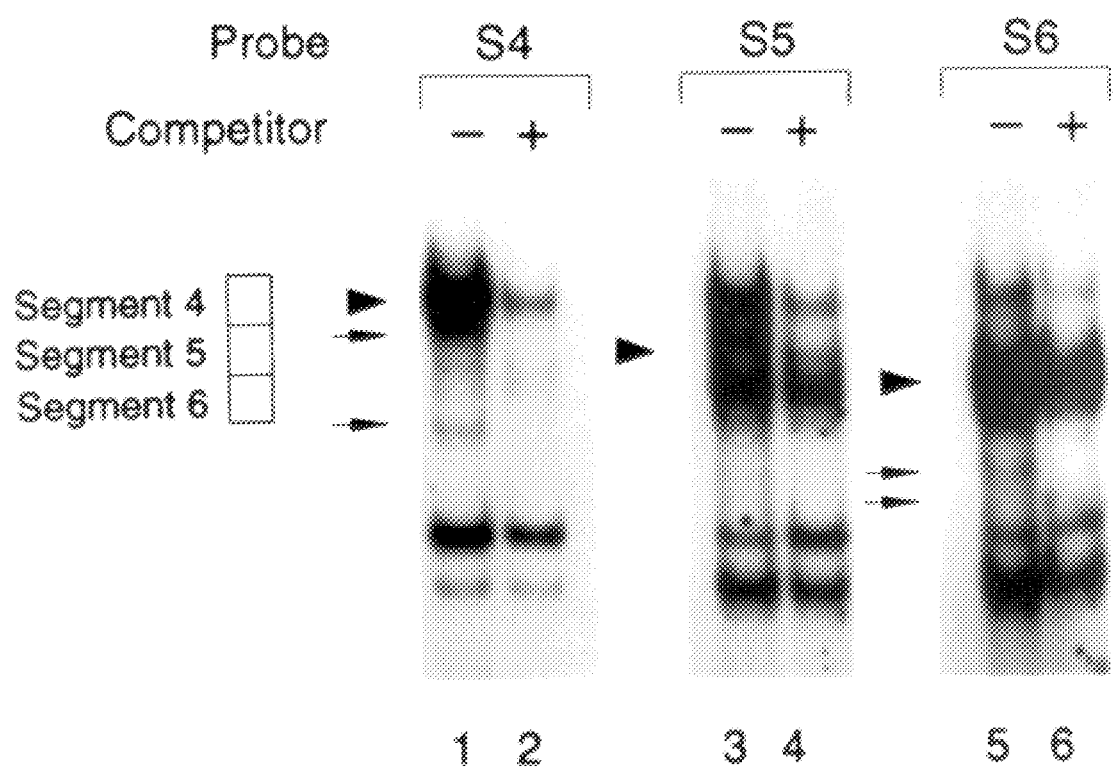
FIG. 2 depicts the analysis of gel segments showing reproducibility of band patterns and reduced complexity.

An analysis of the gel segments shown in FIG. 2 shows reproducibility of band patterns and reduced complexity. To obtain this data, an EMSA experiment was performed using the TP2–4 probes (oligonucleotides selected by four rounds of EMSA using HA-TP2 nuclear extract) and HA-TP2 extract. Shifted oligonucleotides present in a 1 cm length of the lane were isolated and used as probes for the EMSA. The expected complexes corresponding to segments 4, 5, and 6 (represented by boxes in the figure) are marked by arrowheads. Additional complexes are marked by arrows.

Figure 3:
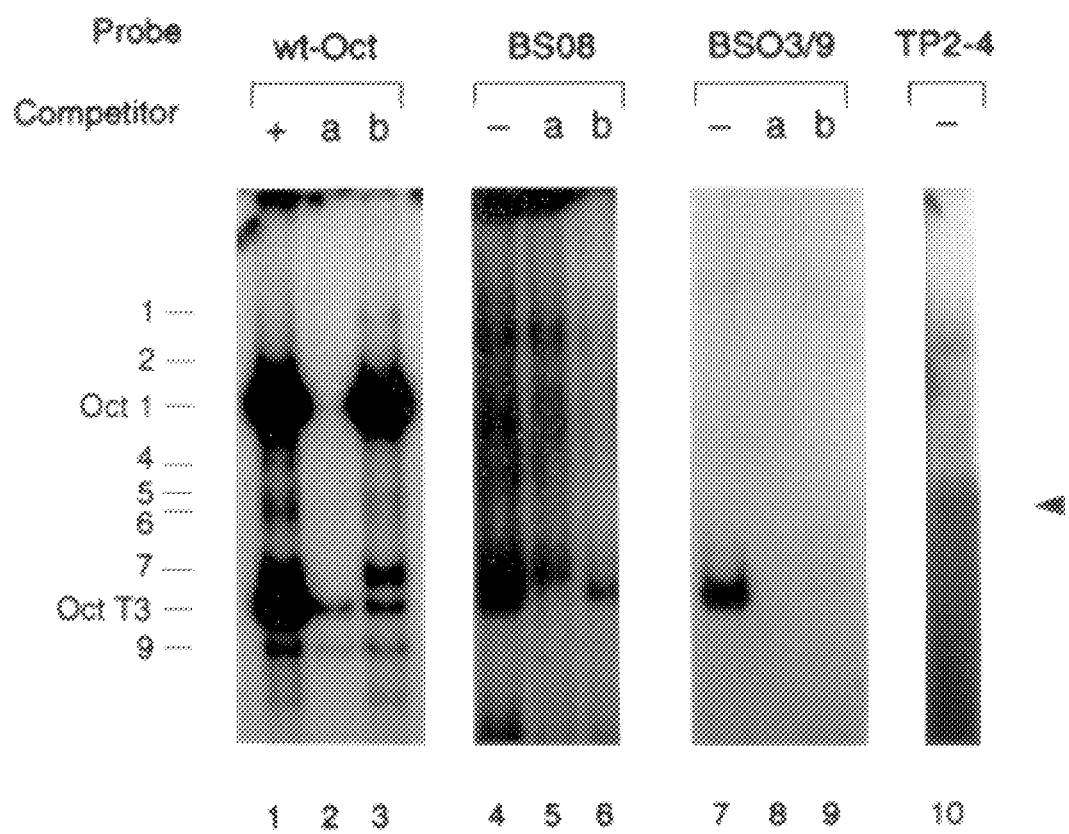
FIG. 3 depicts the isolation of optimal binding sites for Oct-T3.
Figure 4A:
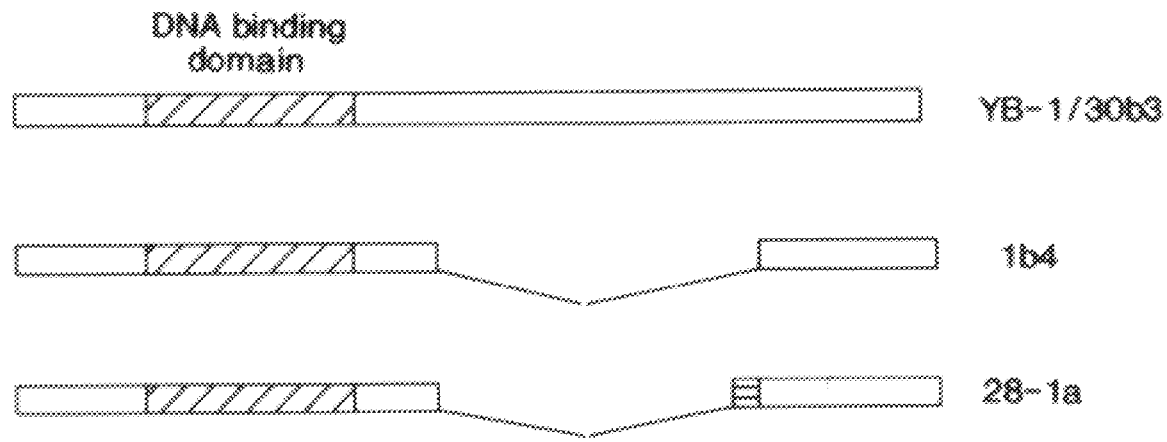
FIG. 4A and 4B depict the structure and binding specificities of the putative Oct-T3 cDNAs.
Figure 4B:
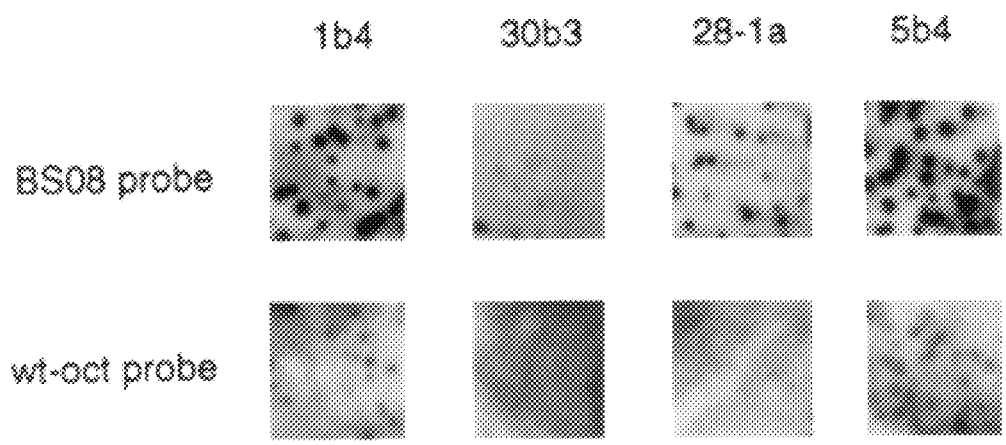

In obtaining the data depicted in FIG. 3, an EMSA experiment was performed using a synthetic wt-Oct duplex probe and HA-TP2 extract, in the presence of competing TP2–4 probes. The region of the EMSA gel corresponding to the Oct-T3 (protein antigenically distinct from Oct1 and Oct2 proteins) band position was excised, amplified by PCR, For the data depicted in FIG. 4, four cDNA clones were isolated by screening a Jurkat cDNA library using southwestern protocols and the BSO8 probe. Clones 30b3 and 5b4 were identical to YB-1, and DBPA genes, respectively. 1b4 and 28-1a are putative splice variants of YB-1 Depicted in FIG. 4B is a comparison of the relative intensities with which the lacZ-fusion polypeptides bind to the BSO8 or wt-Oct probes.

In the present invention, Jurkat cells were grown in RPMI 1640 medium containing 10% (vol/vol) fetal bovine serum and stimulated with either phorbol 12-myristate 13-acetate (PMA), or phytohemagglutinin (PHA) (or both) as described [see Bhargava et al., *Proc. Natl. Acad. Sci. USA* 90:10260 (1993), disclosure of which is incorporated in toto herein]. Very briefly, stimulation occurs in accordance with the procedures of Example I:

EXAMPLE I

Stimulation of Jurkat Cells

Jurkat cells were grown in RPMI 1640 medium containing 10% (vol/vol) fetal bovine serum. Prior to stimulation, the cells were serum-starved in RPMI 1640 medium for 24 hours and replenished with 10% fetal bovine serum at a density of 0.2×106 cells per ml. After 3 hours, either 50 ng of PMA alone or in combination with 2 μg of PHA were added per ml. Cells were harvested at different time intervals, washed with phosphate-buffered saline, and processed for the preparation of RNA or the nuclear protein extracts.

EMSA was done as described [see Fried and Crothers, *Nucleic Acids Res.* 9:6505 (1981)] with a few modifications. Very briefly, EMSA was conducted as in the following Example II:

EXAMPLE II

Electrophoretic Mobility-Shift Assay

A typical binding reaction carried out for 10 min. on ice, contained 1 μl nuclear extract (1.4 μg protein) and 1–2 ng of $^{32}$p labeled probe in a 10 μl reaction containing 1 μg of poly dI-dC. Protein-DNA complexes were fractionated on a 5% acrylamide gel in 0.5×TBE buffer (1×TBE=90 mM Tris/64.6 mM boric acid/2.5 mM EDTA, pH 8.3). Competitions were done with a 40 to 50-fold excess over the probe amounts. Extraction and PCR amplification of oligonucleotide probes from the EMSA gel was performed according to published protocols [see Gruffat and Sergeant, *Nucleic Acids Res.* 22:1172 (1994), the disclosure of which is incorporated in toto herein]. Crude nuclear protein extracts were prepared from resting (HA-R) and activated (HA-TP2) Jurkat cells [see Schreiber et al., *Nucleic Acids Res.* 17:6419 (1989), the disclosure of which is incorporated in toto herein], and these were subsequently fractionated on a heparin-agarose column using published protocols [see Wiederrecht et al., *Cell* 48:507 (1987), the disclosure of which is incorporated in toto herein]. Synthetic oligonucleotides used for the selection rounds contained the sequence 5'-CGAGGTCGACGGTATCGNNNNNNNNNNGGATCCACTAGTTCTAGAGC-3' (Seq. ID No. 7). PCR primers had the sequences, PI, 5'-CGAGGTCGACGGTATCG-3' (Seq ID No. 8), and P2, 5'-GCTCTAGAACTAGTGGATC-3' (Seq. ID No. 9). Four rounds of reiterative selections were performed by EMSA with these oligonucleotides and HA-TP2 extract. The selected oligonucleotides, TP2–4, were subsequently cloned in pBluescript vector to obtain a library of binding sites (TP2–4/BS). Synthetic oligonucleotides used to analyze specific binding sites are BSO8, 5'-GAATAGAACTGGATC-3' (Seq. ID No. 10); BSO3, 5'-ATCGGTAGGKGSGTCGA-3' (Seq. ID No. 11); S6-1, 5'-ACCCCAYACT-3' (Seq. ID No. 12); S6-2, 5'-CCATGATTACR-3' (Seq. ID No. 13); and S6-3, heel primers with Klenow Polymerase, or end-labeled with T4 Polynucleotide Kinase in the presence of 32p nucleotides. The wt-Oct [see Parslow et al., *Proc. Natl. Acad. Sci. USA* 81:2650 (1984), the disclosure of which is incorporated in toto herein] and NFAT [see Flanagan et al., *Nature* 352:803 (1991), the disclosure of which is incorporated in toto herein] probes were also utilized.

For analysis of gel segments, an EMSA experiment was performed with the TP2-4 probes and HA-TP2 extract. A single lane was divided into six 1 cm segments corresponding to the upper third of the gel. Oligonucleotides contained in each segment were separately eluted, amplified, and used for EMSA analysis.

In making the present invention, multiplex selections were used to construct a library of binding sites from activated Jurkat cells. Briefly, synthetic oligonucleotides randomized at 10 contiguous positions and flanked by PCR heels were used as probes for EMSA with nuclear abstracts [see Parslow et al.; supra ]. The portion of the EMSA gel containing bound complexes was excised, the oligonucleotides eluted, and amplified by PCR. An aliquot of the amplified probe was used as the probe for the next cycle of selection by EMSA. After four rounds of selection, the amplified oligonucleotides (TP2–4) were cloned to obtain library of binding sites (TP2–4/BS).

Initially, to evaluate the method, sequences of 20 clones randomly picked from the TP2–4/BS library were obtained and compared with sequences present in the Transcription Factor Database. These sequences are depicted in the following Table I:

TABLE I

| NAME | BINDING SITE | FACTOR | EMSA | SEQ ID No. |
| --- | --- | --- | --- | --- |
| BSN4 | GGACCAATCG | CCAAT-bf[1] | nd* | 16 |
| BSN7 | TGGGTGGGGT | SP1[2] | nd | 17 |
| BSN8 | ACCTGATATA | GATA-1[3] | nd | 18 |
| BSN12 | GTGACTCCCG | TPA Resp Ele[4] | nd | 19 |
| BSN20 | GCCMGGTCG | ELP[5] | nd | 20 |
| BSN15 | CTTTA_CTCG | ANF[6] | Y** | 21 |
| BSN5-1 | CCCATCCATG | Pit-1[7] | N*** | 22 |
| BSN17 | GTAGCCATGT | Pit-1[7] | Y | 23 |
| BSN3 | ATGGTAGCGT | Unknown | N | 24 |
| BSN5-2 | TCGCAATGGG | Unknown | Y | 25 |
| BSN11 | GGTAATAGGN | Unknown | Y | 26 |
| BSN18-3 | CTGGATTATG | Unknown | N | 27 |
| BSN1 | GTGGGGGGTT | Unknown | nd | 28 |
| BSN6 | GTGGGAGGGT | Unknown | nd | 29 |
| BSN9 | CATGGCGGAC | Unknown | nd | 30 |
| BSN12 | GTGACTCCGG | Unknown | nd | 31 |
| BSN13 | GTCTAGGGAG | Unknown | nd | 32 |
| BSN14 | GGGGGGCTAT | Unknown | nd | 33 |
| BSN18-1 | GGGTTATAG | Unknown | nd | 34 |
| 3BSN18-2 | GATTTGGACT | Unknown | nd | 35 |

*indicates that the sequence was not analyzed by EMSA;
**indicates a shift;
***indicates no shift;
[1]see Kingston et al., Mol. Cell Biol. 7:1530 (1987);
[2]see Dynan and Tyran, Nature 316:774 (1985);
[3]see Evans et al., Proc. Natl. Acad. Sci. USA 85:5976 (1988);
[4]see Gee et al., Cell 49:741 (1987);
[5]see Tsukiyamn et al., Mol. Cell Ciol. 9:4670 (1989);
[6]see Herbst et al. Mol Cell Biol. 10:3896 (1990); and
[7]see Elsholtz et al. Genes Dev. 4:43 (1990)

5'-ACCGGAAGYT-3" (Seq. ID No. 14). The S6-1,-2 and -3 oligonucleotides had the specific 10-mer sequence flanked on the 3'-end by the heel sequence 5'-CTTTAGTGAGGGTTAAT-3' (Seq. ID No. 15). Oligonucleotides were labeled either by extension of annealed Similarities with previously known transcription factor binding sites are shown, while those that did not match with sequences in the database have been designated as "unknown".

Among the 20 clones randomly picked from this library, eight binding site sequences resembled those for known transcription factors. Oligonucleotides containing sequences of clones for three known and four unknown sites were selected at random and analyzed by EMSA. Of these, 4 oligonucleotides exhibited specific shifts (FIG. 1). Therefore, by extrapolation, more than two-thirds of the binding sites contained in the library should represent authentic binding sites for DNA binding proteins.

To ascertain that bands extracted from any region of the gel and used as probes in subsequent EMSA experiments would regenerate a band migrating to the original position, an EMSA experiment with the HA-TP2 extract and TP2–4 probes was also prepared. In this experiment, oligonucleotides contained in various segments were extracted and used as probes for analysis by EMSA. As shown in FIG. 2, each probe produced a competable band at the corresponding position (lanes 1 to 6). Most of the segment probes showed additional competable bands revealing the presence of other proteins or protein complexes which bind to the site(s) contained in that gel segment.

Several factors present in T cells have been shown to complex with the wt-Octamer (wt-Oct) sequence [see Bhaugava et al., Supra, Yang et al., *Mol. Cell Biol.* 13:5593 (1993), and Messier et al., *Mol Cell Biol.* 13:5450 (1993)]. The presence of Octamer binding sites was confirmed in the library using bacterially produced Oct2 protein (FIG. 3, lane 10). An EMSA with a synthetic wt-Oct probe and HA-TP2 extract, however, revealed several competable bands (FIG. 3, lanes 1, 2). In particular, we have previously reported on a prominent band, called OctT3, as a protein antigenically distinct from either Oct1 or Oct2 [see Bhargava et al., Supra, and Ullman et al., Science 254:558 (1991)]. However, attempts to clone Oct T3 cDNA(s) by screening expression libraries in bacteria with a multimerized wt-Oct probe were unsuccessful, although other cDNAs encoding proteins that specifically bind to the wt-Oct site were isolated. Therefore, alternative approaches were taken to clone cDNA(s) corresponding to the OctT3 EMSA band.

It was likely that the OctT3 activity might be associated fortuitously with the wt-Oct probe, and that other preferred sites for OctT3 existed. If so, then such sites should have been selected during the random oligonucleotide selections with total nuclear extract and should be represented in the library of binding sites. Therefore, high affinity binding sites for OctT3 were extracted from the TP2–4 probes by competition of the OctT3-wt-Oct complex. The resulting probe mixture strongly competed the OctT3 band and also bands 4 and 6 in subsequent EMSA with the wt-Oct probe. Upon cloning and sequencing 9 clones from this probe mixture, 5 clones contained the A-T rich sequence 5'-AATAGAA-3' (BSO8) (Seq. ID No. 36), while 3 others were a set of G-C rich sequences that showed the consensus pattern 5'-TAGGDGBAGGG-3' (BSO3/9) (Seq. ID No. 37). The BSO8 probe strongly competed the OctT3 band and bands 4 and 6, but not other bands seen with the wt-Oct probe (FIG. 3, lane 3). Several complexes were seen when BSO8 itself was used as probe (lane 4) that were competed by excess BSO8 (lane 6), but only partially by the wt-Oct probe (lane 5). The BSO3/9 EMSA pattern consisted of a single prominent band in the position of a major band of the BSO8 pattern (FIG. 3, compare lanes 4 and 7). Nevertheless, BSO3/9 binding was competed by the BSO8 probe as well as the wt-Oct duplex (FIG. 3, lanes 8 and 9, respectively), suggesting that factors that bind to the BSO3/9 probe could be a subset of those that bind to the BSO8 probe. Taken together, these results showed that the BSO8 binding site was selected from the library in preference to the wt-Oct sequence. This finding strongly suggests that BSO8 is an optimal binding site for the OctT3 protein.

In view of these findings, a Jurkat cDNA library in λ-gt11 [see Vinson et al., *Genes Dev.* 2:801 (1988)] was screened with the BSO8 probe. From this screening, four cDNAs were isolated, all of which were members of a family of transcription factors termed the Y-box binding proteins. One of the clones, 30b3 was identical to YB-1 [see Didier et al., *Proc. Natl. Acad. Sci. USA* 85:7322 (1988)]. Two other clones were presumptive splice variants of the YB-1 cDNA (FIG. 4a). Clone 1b4 lacked 96 internal amino acids in the C-terminus (from residues 158 through to 245 of YB-1 as depicted in Didier et al., Supra, while clone 28-1a lacked 108 amino acids (from residue 158 through to 256). Clone 5b4 was identical to the dbpA gene [see GeneBank Accession No. M24069]. These findings strongly indicate that OctT3 is a member of the Y-box family of transcription factors.

A comparison of the relative intensities with which the lacZ-fusion proteins bound the BSO8 and wt-Oct probes (FIG. 4B) confirmed that the BSO8 probe is a preferred binding site over the wt-Oct probe. Due to the low affinities of the lacZ-fusion proteins for the wt-Oct probe, they may easily have gone undetected in previous screens with the octamer probe. The isolation of an optimal binding site for OctT3 using the approach described herein alleviated this problem and permitted their cloning and ultimate identification.

Figure 5:
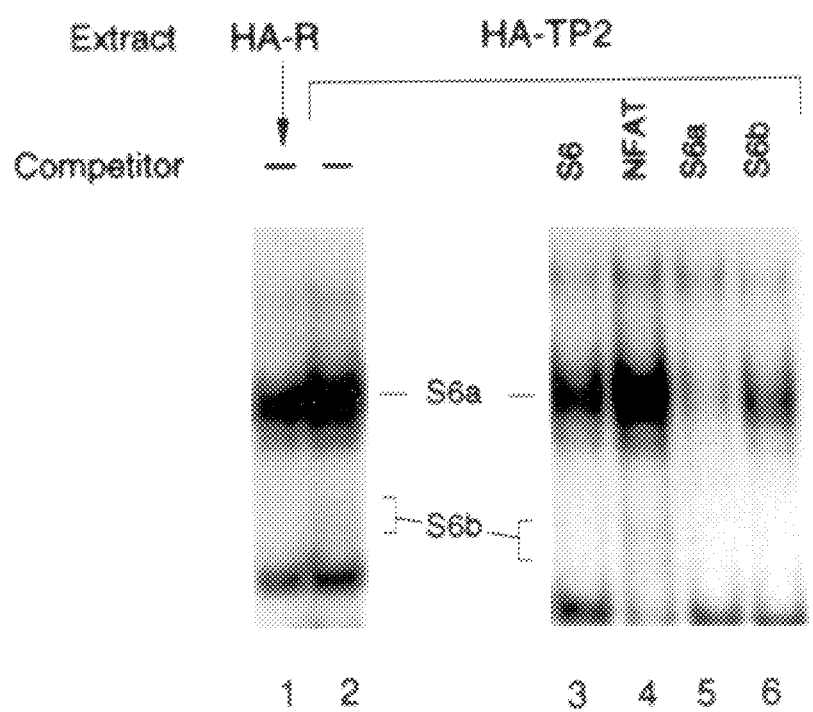
FIG. 5 depicts the appearance of additional Ets-like binding activities in Jurkat cells treated with PMA/PHA and FIG. 6 depicts the competition of the S6b binding activity by the synthetic S6-3 consensus probe.

A subset of the library probes was next employed to compare differences in factor binding activities In quiescent and activated Jurkat cells. The segment 6 (S6) probe showed two additional bands, called S6b, with the HA-TP2 extract (FIG. 5, lane 2) that were absent with extracts from quiescent Jurkat cells (lane 1). These bands were competed by excess of total S6 material (lane 3), and also by the extracted S6a probe(s) (lane 5). The S6b probe, however, competed the S6b bands efficiently, but only partially competed the S6a complex (lane 6), suggesting that band S6a could contain more than one comigrating DNA-protein complex.

The N-FAT binding site [see Flanagan et al., Supra] is known to be activated early during T cell activation. However, the N-FAT binding site did not compete any of the specific bands in the S6 probe (lane 4). Although, when used as a probe in EMSA, it showed specific shifts that were competed by excess of unlabeled N-FAT duplex but not by the total S6 material. This indicates that the S6b binding activities in activated nuclear extracts are distinct from those of N-FAT.

Sequences from 30 clones contained in the S6 probe are listed in the following Table 2 (wherein core nucleic acid sequences are indicated in boldface type and nucleic acids originating from the heel are indicated in italic letters). They fall into three different consensus patterns: 13 conformed to the consensus pattern, RTGGGBGGRY, (S6-1) (Seq. ID No. 51); 8 to the consensus pattern YT/GRTAAA/CC/G (i.e., YKRTAAMS) (S6-2) (Seq. ID No. 60), and 5, to the consensus pattern A/TCCGGAAGY (I.E., WCCGGAAGY) (S6-3) (Seq. ID No. 66).

TABLE 2

| clone | Sequence | SEQ ID No. |
|---|---|---|
| 6-2-2 | GGGGATGGGCGGATCC | 38 |
| 6-3-1 | TAGTGTGGGTGGATCC | 39 |

TABLE 2-continued

| clone | Sequence | SEQ ID No. |
|---|---|---|
| 6-3-3 | ATTTATGGGGGGATCC | 40 |
| 6-5-1 | GTAGGTGGGCGGATCC | 41 |
| 6-5-3R | CGGAAGTGGCCGATACC | 42 |
| 6-6-1 | GACACGTGATGGATCC | 43 |
| 6-6-3 | TATGGGGGAA | 44 |
| 6-7-1 | GTGGGTGGGC | 45 |
| 6-9-1 | GATTATGGGTGGATCC | 46 |
| 6-9-3 | GGTTGGGGGC | 47 |
| 6-11-2R | GTGGGCGGGG | 48 |
| 6-12-2R | GTGGGGGCTC | 49 |
| 6-12-3 | TGTCGTGGGTGGATCC | 50 |
| consensus | pattern (S6-1)   RTGGGBGGRY | 51 |
| 6-1 | AATTGTAAGC | 52 |
| 6-2-1 | TTAGGTAAAT | 53 |
| 6-5-2 | CGCTGTAATA | 54 |
| 6-6-2R | CCGTAAAGGG | 55 |
| 6-7-5R | GCCTATAACG | 56 |
| 6-9-2 | GGGATAAACGC | 57 |
| 6-10-1R | CATCTAACC | 58 |
| 6-10-2 | CATCATAACC | 59 |
| consensus | pattern (S6-2)   YKRTMMS | 60 |
| 6-3-2R | AACCGGAAGT | 61 |
| 6-4-1R | CGTACCGGAAGG | 62 |
| 6-8 | TCCGGAAGC | 63 |
| 6-11-1 | TCCGGAAGC | 64 |
| 6-11-3 | ACCGGAAGT | 65 |
| consensus | pattern (S6-3)   WCCGGGAGY | 66 |

Figure 6:
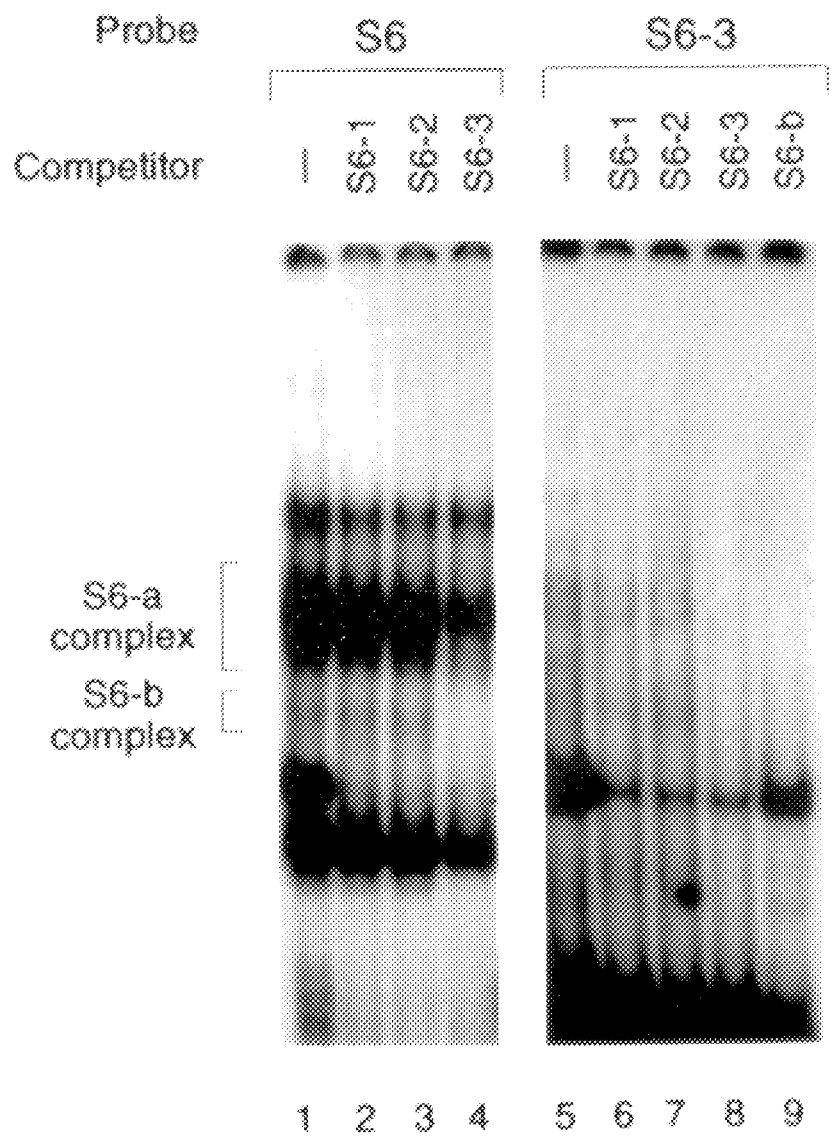

Synthetic oligonucleotides containing the consensus core sites were used in the EMSA analysis. The S6-3 synthetic oligonucleotide duplex, but not S6-1 or S6-2, competed with the S6b bands (FIG. 6, lane 4). Conversely, the shifts produced by the synthetic S6-3 probe were competed equally well by S6-3 and S6b (FIG. 6, lanes 8 and 9 respectively), but not by the other synthetic probes, indicating that the S6b bands seen when using activated extracts were due to the S6-3 consensus sequence. Comparison of the S6-3 consensus sequence with the databases revealed striking homologies with binding sites for the Ets family of transcription factors [see Faisst and Meyer, *Nucleic Acids Res.* 20:3 (1992), and Wong et al., *J. Exp. Med.* 175:1391 (1992)].

In summary, several approaches for the selection of random oligonucleotides have been described that were aimed at determining the target recognition sites of DNA-binding proteins [see Irvine et al., *J. Mol. Biol.* 222:739 (1991), Blackwell and Weintraub, *Science* 250:1104 (1990), and Thieson and Bach, *Nucleic Acids Res.* 18:77 (1990)]. These methods have involved the use of single target macromolecules or nucleic acids for selection of totally or partially randomized oligonucleotides isolated by a variety of methods that include immunoprecipitation, filter binding, binding to affinity columns, isolation of bands by EMSA, or Southwestern blotting. The consensus DNA binding sites for several proteins have been determined using these approaches [see Wright and Funk, *Trends Biochem. Sci.* 18:77 (1993)]. A somewhat different approach, i.e., CASTing [see Funk and Wright, *Proc. Natl. Acad. Sci. USA* 89:9484 (1992)], has been used to identify transcription factors that bind adjacent to, and cooperate with, a specific factor for which an antibody is available. In CASTing, a crude nuclear extract is mixed with an amplifiable mixture of oligonucleotides containing a rather large (35 base pairs) randomized segment. Binding oligonucleotides are selected by immunoprecipitation and reamplified. With this approach, evidence was obtained for consensus binding sites for at least six factors with which myogenin interacts.

The goal and protocols of the approach taken described herein differ from prior approaches in that the present invention is designed to obtain the optimal binding sites for multiple factors simultaneously without prior knowledge of the factors. The present approach differs from the prior techniques in the dynamics of the random oligonucleotide selections, end-point analysis, and applications for the selected material. Since several independent DNA-protein interactions occur simultaneously in this approach, we have termed it the Multiplex Selection Technique, or MuST.

The enrichment of specific binding sites is determined by various criteria, in particular, the dissociation constant, relative ratios of factor to probe, and the size of sequence recognized. Success in selecting the highest affinity sites is largely dependent upon the use of optimum conditions that define the ratio of specific to non-specific sites selected for each interaction. The condition that favors selection of preferred sites is one that maintains the concentration of specific probes at or below the association constant for the complex between probe and target protein so that there will be good discrimination between optimum and suboptimum binding sites, even in the presence of an excess of the target protein.

The molar concentrations of an asymmetric 10-mer binding site in the experiments reported herein was $5 \times 10^{-15}$; for a 6-mer it is $5 \times 10^{-12}$; while that of protein is estimated at $3.5 \times 10^{-10}$M, (for a protein of 40 kD, that may be present in the extracts at an abundance level of 1:10,000 with respect to the total mass of protein). Under these conditions, the concentration of probe and a single protein will be well below the average Kd values (assumed to be $10^{-8}$) even for small binding sites. Therefore, the binding of any target is not driven to saturation of either the probe or protein, thus permitting discrimination of optimal and sub-optimal sites. At the same time, because there are multiple protein targets in the same mixture, the total amount of oligonucleotide selected specifically by some protein will be relatively high compared to the background of non-specifically retained probe. The ratios of binding sites selected by two proteins will be determined by the mathematical equation $$[(P_1/P_2)(K_1/K_2)]^n$$

wherein $P_1$ and $P_2$, $K_1$ and $K_2$ are their respective concentrations and binding constants, and "n" is the number of cycles of selection (as indicated in the flow sequence given above, 4 cycles were selected in collecting the data that led to the making of the present invention; however, the exact number of cycles will be a matter of choice depending upon the degree of selection desired and the constraints placed upon the amount of material needed in the final selection; the 4 cycles used herein were found to be optimum for the material under study in the embodiment described herein). In view of the large number of binding proteins, the total ratio of specific to non-specifically retained oligonucleotides will be relatively high at each cycle, and only a limited number of cycles of selection are needed to get a library in which most oligonucleotides represent specific binding sites.

By using relatively short random oligonucleotides in the protocol according to the present invention, the chance of selecting oligonucleotides that contain separate binding sites for two different proteins was decreased. This avoids information or confusion about interaction between proteins separately bound to DNA, but increases the likelihood of obtaining a single optimal site for each protein. In turn, this simplifies the analysis of data and cataloging of DNA binding sites.

The sequences of particular binding activities examined herein showed a small number of extended binding sites rather than a wide spread of sub-optimal sites (Table 2). The use of native proteins in the present approach, as in the prior CASTing technique, has advantages over using exogenously synthesized proteins, for post-translational modifications and accessory protein factors may modify the stringency and selectivity of some DNA binding proteins. Complexing with other factors have been demonstrated to alter the DNA-binding specificities of transcription factors; and it might also be envisaged that protein-protein interactions might create a protein DNA interaction motif, where neither partner may bind to DNA independently, or that such interaction might stabilize binding by any factor.

At a minimum, eight of twenty clones picked at random from the library of binding sites resembled recognition sites for known transcription factors. In particular, we found two sequences that resembled binding sites for Pit-1, a POU-homeodomain transcription factor that is preferentially expressed in the pituitary gland [see Lew and Elsholtz, *Nucleic Acids Res.* 19:6329 (1991)] and that has recently also been detected in hematopoietic and lymphoid cells [see Delhase et al., *Eur. J. Immunol* 23:951 (1993)]. A third sequence resembled the binding site for ANF, a factor that negatively regulates the albumin enhancer in hepatocytes [see Hertist et al., *Mol. Cell. Biol.* 10:3896 (1990)], and whose presence in T cells has not been demonstrated prior to this disclosure. In view of this, an EMSA analysis of these three sites and four other sites that did not match with sequences in various scientific databases was conducted. BSN17, one of the Pit-1-like sites, exhibited two complexes in Jurkat cells (FIG. 1), but a single complex in JY cells, thereby revealing the presence in lymphoid cells of Pit-1-like binding activities. The ANF-like site showed a single complex. Furthermore, two of the four previously unknown sites showed specific shifts. Taken together, these data indicate that at least 70% of the DNA probes contained in the binding site library represent demonstrable binding sites, and thereby will facilitate cloning of additional factors from, especially, activated Jurkat cells.

Accurate estimation of the total complexity of binding sites in the library was not possible. However, the low level of even imperfect repeats of binding site sequences in randomly sequenced clones suggests that hundreds of sites are most likely represented. Also, when multiple clones with the same binding site were sequenced, as in the case of the Ets-like sequences, the structure of individual clones was all different, thus indicating that clones were not selectively amplified from an extremely small pool by a "Monte Carlo" effect, i.e., the observation that in PCR reactions with very small amounts of total template, one may see at times random, marked amplification of one or another template compared with the remaining potential templates in a mixture.

Non-specific interactions might arise due to binding of single or double stranded DNA, ends of DNA molecules, or hairpin loops of DNA molecules by proteins present in the nuclear extracts. However, the large excess of poly dI:dC and the use of Heparin agarose fractionated nuclear extracts might have reduced these interactions to some extent. Non-specific interactions that might arise by the formation of 'bubbles' during PCR were minimized in these studies leading to the present invention by preparing probes by extension of annealed primers with Klenow polymerase.

Some of the intense bands that appear during the selection rounds could be due to the PCR heels contributing to binding sites. Certain intense bands were seen with one set of heels but not a second set, and vice versa. Changing PCR heels after two rounds of selection with one set of heels by recloning with a second set of heels may overcome this effect to some extent. To avoid non-specific interactions the PCR heels could be partially digested away with restriction endonucleases. The PCR heels may also contribute in part to the binding sites. In the data presented herein, one set of sequences, S6-1 (Table 2 wherein the heel sequences appear in italics), almost certainly involved partial binding to the PCR heels, as the synthetic core site did not exhibit EMSA shifts in the absence of the heel sequence.

As described herein, the present invention allowed for the isolation of a mixture of binding sites that strongly competed the OctT3 EMSA band produced with a wild-type octamer (wt-Oct) probe. These sequences were then used to isolate cDNA clones of the Y box family, a group of proteins previously cloned because of their interaction with the Y box of the human MHC Class II DRA chain promoter [see Didier et al., *Proc. Natl. Acad. Sci. USA* 85:7322 (1988)]. The sequences then isolated were categorized into two consensus patterns as described above, an A-T rich set (BSO8) similar to the sequences in and flanking the Y-box, and a G-C rich set (BSO3/9) homologous to sequences in and flanking the adjacent X box of the DRA promoter. The reason(s) for seeing multiple EMSA complexes with the BSO8 probe and only a single complex with the BSO3/9 probe are presently unclear. However, recently, YB-1 was shown to bind to regions of the X-box and the Y-box [see MacDonald et al., *J. Biol. Chem.* 270:3527 (1995)], and curiously, a consensus octamer site is present adjacent to the Y-box motif in the DRA promoter, which may account in part for the multiple EMSA complexes.

Data obtained strongly suggest that the OctT3 activity could be a member of the 'cold-shock' family of transcription factors, and quite possibly be YB-1. The successful cloning of the OctT3 binding activity by the protocols employed herein, clearly demonstrates the selectivity of the present invention for naturally occurring sites, and also the ease with which binding sites can be extracted from an appropriate library when specific criteria are employed. The finding that the BSO8 probe bound more strongly than the wt-Oct probe to the lacZ polypeptides reconfirms the presence of optimal probes in the library and validates the MuST method.

Partitioning the library probes into gel segments has facilitated more detailed analysis by decreasing the complexity. With some exceptions, the pattern of bands with any segment probe was identical in resting and activated Jurkat nuclear extracts. Segment 6, however, showed additional bands in activated as compared to the resting extracts. The absence of competition of the S6 bands by a synthetic N-FAT site and their sequence analyses suggested that other factor(s) might be involved. These differences were consistently observed in duplicate experiments, with extracts prepared at different times, and in heparin agarose fractionated as well as crude nuclear extracts from activated Jurkat cells. EMSA experiments with synthetic S6 consensus sites showed that the binding site responsible for the S6b activity, in fact, resembles a reported Ets binding site [see Faisst and Meyer, *Nucleic Acids Res.* 20:3 (1992)].

A large family of Ets-like transcription factors have been described. Ets-1 and Ets-2 are expressed at high levels in T cells. Another set of Ets proteins comprise the Tenary Complex Factors [see Price et al,. *EMBO J.* 14:2589 (1995)], Elk-1, Sap-1a, and Sap-2, that remain associated with the c-fos SRE even in unstimulated cells; transcriptional activation by these is potentiated by phosphorylation in response to serum, v-ras, PMA, and other agents. Elf-1, a T cell-specific Ets protein, has been demonstrated to be involved in the expression of a number of genes. Although inducible by mitogens in peripheral T cells, Elf-1 expression was found to be constitutive in Jurkat and other lymphoid cell lines. One component of the S6a band found in the present invention is a constitutively expressed factor, whose relative mobility in EMSA gels is consistent with the molecular size of Elf-1. The S6b bands, however, may represent yet unidentified members of the Ets family. Ets-like activities with comparable mobilities in EMSA gels to the S6b complexes have been observed although their inducible nature was not apparent. These complexes were not super-shifted by antisera to either Ets-1, Elf-1, GABPα, or GABPβ, suggesting that the techniques described herein have located additional, previously unknown, members of the Ets family of transcription factors in T cells.

Utilizing the present invention, it becomes readily apparent to those skilled in the art that other cell type specific binding site libraries may be prepared by subtraction in EMSA. Alternatively, it is also readily apparent that consensus binding site sequences derived from a statistical analysis resulting from large scale sequencing of binding sites from a single library may be used to determine cell type-specificity of DNA recognition sites by the techniques of the present invention.

A priori, one might have expected an overwhelmingly complex pattern in experiments utilizing the described MuST invention because of the number of transcription factors, alternative splices, complexes of several proteins, etc. However, as shown herein, the actual pattern is workable with relative ease. More importantly, since a large number of transcription factors can be analyzed en masse in a single study, the present invention offers the investigator rapid insights into the distribution of factors in the cell type and to identify particular factors for further study, while simultaneously generating optimal probes for cloning the specific factor.

As mentioned above, the essential beauty of the MuST procedure is that by using a complex mixture of targets in the selection steps one can, in a relatively small number of selection cycles, obtain a mixture predominantly made up of specific probes containing optimal sequences. By starting with two (i.e., probes and targets) complex 1 0 mixtures, one can obtain a high ratio of specifically retained material to non-specific background in the early cycles, without working with concentrations of probe or target such that large amounts of more weakly binding material is retained. This is shown, for example, in applying the MuST invention to a selection of antibody expressing phages. For example, using this system, we have been able to use a crude nuclear extract or a complex of a long DNA probe with multiple binding proteins attached, and enrich more phage from a general library than could be recovered using a single protein as a target. In this instance, the probes are represented by individual phage particles rather than oligonucleotides, and the mode of separation of complexed from uncomplexed probes is to immobilize the target proteins (for example, on a plastic surface) and wash off unbound phage. The equilibrium considerations and advantages of the multiplex approach with the phage system are essentially the same as when oligonucleotides are used as probes as specifically described herein.

Thus, while we have illustrated and described the preferred embodiment of our invention, it is to be understood that this invention is capable of variation and modification, and should therefore not be limited to the precise terms set forth, but include such changes and alterations which may be made for adapting the invention to various usages and conditions. For example, while the specific embodiments described herein utilize Jurkat T cells because of their acceptability by the scientific community as a model for other cell types, it is to be understood that other embodiments may utilize other cell types. Furthermore, while specific chemicals are named herein for the activation of cells, it is to be understood that whenever a cell is brought into contact with an exogenous material, such as for example a pharmaceutical or toxic compound, the cell will invariably provide some genetic response to the material resulting in changes in transcription factors. These changes can also be noted using the present invention with very little alteration to the general scheme of the method depicted herein, and these changes can be used to evaluate the effect that such materials have on the host cell that has been exposed to the material. As still another modification within the scope of the present invention is the binding of either the target or probe molecules to a solid support, as for example, various plastic materials, silica gels, or controlled pore glass in order to provide a means to aid in the of automation of the disclosed MuST invention. Accordingly, such changes, modifications, alterations and uses are properly intended to be within the full range of equivalents, and therefore within the purview of the following claims.

A complete listing of all nucleotide sequences described in the above description of the present invention follows:

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
        ( A ) LENGTH: 8 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:1:

ATGCAAAT                                                                                              8

( 2 ) INFORMATION FOR SEQ ID NO:2:

( i ) SEQUENCE CHARACTERISTICS:
        ( A ) LENGTH: 6 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:2:

AATCAG                                                                                                6

( 2 ) INFORMATION FOR SEQ ID NO:3:

( i ) SEQUENCE CHARACTERISTICS:
        ( A ) LENGTH: 4 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:3:

CTAG                                                                                                  4

( 2 ) INFORMATION FOR SEQ ID NO:4:

( i ) SEQUENCE CHARACTERISTICS:
        ( A ) LENGTH: 8 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:4:

ATGCAAAT                                                                                              8

( 2 ) INFORMATION FOR SEQ ID NO:5:

( i ) SEQUENCE CHARACTERISTICS:
        ( A ) LENGTH: 7 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:5:

AATAGAA                                                                                               7

( 2 ) INFORMATION FOR SEQ ID NO:6:

( i ) SEQUENCE CHARACTERISTICS:
        ( A ) LENGTH: 68 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:6:

ATGCAAATNN   NNNNNNNNNN   NNNNAATCAG   AANNNNNNNN   NNNNNNNNNN                      50

NNNNNNNNCT   AGGGGGGG                                                                            68

( 2 ) INFORMATION FOR SEQ ID NO:7:

( i ) SEQUENCE CHARACTERISTICS:
        ( A ) LENGTH: 47 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:7:

CGAGGTCGAC GGTATCGNNN NNNNNNGGA TCCACTAGTT CTAGAGC    47

( 2 ) INFORMATION FOR SEQ ID NO:8:

( i ) SEQUENCE CHARACTERISTICS:
        ( A ) LENGTH: 17 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:8:

CGAGGTCGAC GGTATCG    17

( 2 ) INFORMATION FOR SEQ ID NO:9:

( i ) SEQUENCE CHARACTERISTICS:
        ( A ) LENGTH: 19 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:9:

GCTCTAGAAC TAGTGGATC    19

( 2 ) INFORMATION FOR SEQ ID NO:10:

( i ) SEQUENCE CHARACTERISTICS:
        ( A ) LENGTH: 15 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:10:

GAATAGAACT GGATC    15

( 2 ) INFORMATION FOR SEQ ID NO:11:

( i ) SEQUENCE CHARACTERISTICS:
        ( A ) LENGTH: 17 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:11:

ATCGGTAGGK GSGTCGA    17

( 2 ) INFORMATION FOR SEQ ID NO:12:

( i ) SEQUENCE CHARACTERISTICS:
        ( A ) LENGTH: 10 base pairs
        ( B ) TYPE:nucleic acid (C) STRANDEDNESS:single
            (D) TOPOLOGY:linear (ii) MOLECULE TYPE:DNA (xi) SEQUENCE DESCRIPTION: SEQ ID NO:12:

ACCCCAYACT                                                                                              10

(2) INFORMATION FOR SEQ ID NO:13:

(i) SEQUENCE CHARACTERISTICS:
            (A) LENGTH: 11 base pairs
            (B) TYPE:nucleic acid
            (C) STRANDEDNESS:single
            (D) TOPOLOGY:linear (ii) MOLECULE TYPE:DNA (xi) SEQUENCE DESCRIPTION: SEQ ID NO:13:

CCATGATTAC R                                                                                            11

(2) INFORMATION FOR SEQ ID NO:14:

(i) SEQUENCE CHARACTERISTICS:
            (A) LENGTH: 10 base pairs
            (B) TYPE:nucleic acid
            (C) STRANDEDNESS:single
            (D) TOPOLOGY:linear (ii) MOLECULE TYPE:DNA (xi) SEQUENCE DESCRIPTION: SEQ ID NO:14:

ACCGGAAGYT                                                                                              10

(2) INFORMATION FOR SEQ ID NO:15:

(i) SEQUENCE CHARACTERISTICS:
            (A) LENGTH: 17 base pairs
            (B) TYPE:nucleic acid
            (C) STRANDEDNESS:single
            (D) TOPOLOGY:linear (ii) MOLECULE TYPE:DNA (xi) SEQUENCE DESCRIPTION: SEQ ID NO:15:

CTTTAGTGAG GGTTAAT                                                                                      17

(2) INFORMATION FOR SEQ ID NO:16:

(i) SEQUENCE CHARACTERISTICS:
            (A) LENGTH: 10 base pairs
            (B) TYPE:nucleic acid
            (C) STRANDEDNESS:single
            (D) TOPOLOGY:linear (ii) MOLECULE TYPE:DNA (xi) SEQUENCE DESCRIPTION: SEQ ID NO:16:

GGACCAATCG                                                                                              10

(2) INFORMATION FOR SEQ ID NO:17:

(i) SEQUENCE CHARACTERISTICS:
            (A) LENGTH: 10 base pairs
            (B) TYPE:nucleic acid
            (C) STRANDEDNESS:single
            (D) TOPOLOGY:linear (ii) MOLECULE TYPE:DNA ( x i ) SEQUENCE DESCRIPTION: SEQ ID NO:17:

TGGGTGGGGT 10

( 2 ) INFORMATION FOR SEQ ID NO:18:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:18:

ACCTGATATA 10

( 2 ) INFORMATION FOR SEQ ID NO:19:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:19:

GTGACTCCCG 10

( 2 ) INFORMATION FOR SEQ ID NO:20:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:20:

GCCAAGGTCG 10

( 2 ) INFORMATION FOR SEQ ID NO:21:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:21:

CTTTACTCG 9

( 2 ) INFORMATION FOR SEQ ID NO:22:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:22:

CCCATCCATG 10

( 2 ) INFORMATION FOR SEQ ID NO:23:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:23:

GTAGCCATGT         10

( 2 ) INFORMATION FOR SEQ ID NO:24:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:24:

ATGGTAGCGT         10

( 2 ) INFORMATION FOR SEQ ID NO:25:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:25:

TCGCAATGGG         10

( 2 ) INFORMATION FOR SEQ ID NO:26:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:26:

GGTAATAGGN         10

( 2 ) INFORMATION FOR SEQ ID NO:27:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:27:

CTGGATTATG         10

( 2 ) INFORMATION FOR SEQ ID NO:28:

( i ) SEQUENCE CHARACTERISTICS:
        ( A ) LENGTH: 10 base pairs
        ( B ) TYPE:nucleic acid (C) STRANDEDNESS:single
        (D) TOPOLOGY:linear (ii) MOLECULE TYPE:DNA (xi) SEQUENCE DESCRIPTION: SEQ ID NO:28:

GTGGGGGGTT                                                                                              10

(2) INFORMATION FOR SEQ ID NO:29:

(i) SEQUENCE CHARACTERISTICS:
        (A) LENGTH: 10 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:29:

GTGGGAGGGT                                                                                              10

(2) INFORMATION FOR SEQ ID NO:30:

(i) SEQUENCE CHARACTERISTICS:
        (A) LENGTH: 10 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:30:

CATGGCGGAC                                                                                              10

(2) INFORMATION FOR SEQ ID NO:31:

(i) SEQUENCE CHARACTERISTICS:
        (A) LENGTH: 10 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:31:

GTGACTCCCG                                                                                              10

(2) INFORMATION FOR SEQ ID NO:32:

(i) SEQUENCE CHARACTERISTICS:
        (A) LENGTH: 10 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:32:

GTCTAGGGAG                                                                                              10

(2) INFORMATION FOR SEQ ID NO:33:

(i) SEQUENCE CHARACTERISTICS:
        (A) LENGTH: 10 base pairs
        (B) TYPE:nucleic acid
        (C) STRANDEDNESS:single
        (D) TOPOLOGY:linear (ii) MOLECULE TYPE:DNA ( x i ) SEQUENCE DESCRIPTION: SEQ ID NO:33:

GGGGGGCTAT                                                                                                          10

( 2 ) INFORMATION FOR SEQ ID NO:34:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:34:

GGGTTATAG                                                                                                            9

( 2 ) INFORMATION FOR SEQ ID NO:35:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:35:

GATTTGGACT                                                                                                          10

( 2 ) INFORMATION FOR SEQ ID NO:36:

( i ) SEQUENCE CHARACTERISTICS:
        ( A ) LENGTH: 7 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:36:

AATAGAA                                                                                                              7

( 2 ) INFORMATION FOR SEQ ID NO:37:

( i ) SEQUENCE CHARACTERISTICS:
        ( A ) LENGTH: 11 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:37:

TAGGDGBAGG G                                                                                                        11

( 2 ) INFORMATION FOR SEQ ID NO:38:

( i ) SEQUENCE CHARACTERISTICS:
        ( A ) LENGTH: 16 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:38:

GGGGATGGGC GGATCC                                                                                                   16

( 2 ) INFORMATION FOR SEQ ID NO:39:

( i ) SEQUENCE CHARACTERISTICS:
        ( A ) LENGTH: 16 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:39:

TAGTGTGGGT GGATCC     16

( 2 ) INFORMATION FOR SEQ ID NO:40:

( i ) SEQUENCE CHARACTERISTICS:
        ( A ) LENGTH: 16 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:40:

ATTTATGGGG GGATCC     16

( 2 ) INFORMATION FOR SEQ ID NO:41:

( i ) SEQUENCE CHARACTERISTICS:
        ( A ) LENGTH: 16 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:41:

GTAGGTGGGC GGATCC     16

( 2 ) INFORMATION FOR SEQ ID NO:42:

( i ) SEQUENCE CHARACTERISTICS:
        ( A ) LENGTH: 17 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:42:

CGGAAGTGGC CGATACC     17

( 2 ) INFORMATION FOR SEQ ID NO:43:

( i ) SEQUENCE CHARACTERISTICS:
        ( A ) LENGTH: 16 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:43:

GACACGTGAT GGATCC     16

( 2 ) INFORMATION FOR SEQ ID NO:44:

( i ) SEQUENCE CHARACTERISTICS:
        ( A ) LENGTH: 10 base pairs
        ( B ) TYPE:nucleic acid (C) STRANDEDNESS:single
(D) TOPOLOGY:linear (ii) MOLECULE TYPE:DNA (xi) SEQUENCE DESCRIPTION: SEQ ID NO:44:

TATGGGGGAA 10

(2) INFORMATION FOR SEQ ID NO:45:

(i) SEQUENCE CHARACTERISTICS:
(A) LENGTH: 10 base pairs
(B) TYPE:nucleic acid
(C) STRANDEDNESS:single
(D) TOPOLOGY:linear (ii) MOLECULE TYPE:DNA (xi) SEQUENCE DESCRIPTION: SEQ ID NO:45:

GTGGGTGGGC 10

(2) INFORMATION FOR SEQ ID NO:46:

(i) SEQUENCE CHARACTERISTICS:
(A) LENGTH: 16 base pairs
(B) TYPE:nucleic acid
(C) STRANDEDNESS:single
(D) TOPOLOGY:linear (ii) MOLECULE TYPE:DNA (xi) SEQUENCE DESCRIPTION: SEQ ID NO:46:

GATTATGGGT GGATCC 16

(2) INFORMATION FOR SEQ ID NO:47:

(i) SEQUENCE CHARACTERISTICS:
(A) LENGTH: 10 base pairs
(B) TYPE:nucleic acid
(C) STRANDEDNESS:single
(D) TOPOLOGY:linear (ii) MOLECULE TYPE:DNA (xi) SEQUENCE DESCRIPTION: SEQ ID NO:47:

GGTTGGGGGC 10

(2) INFORMATION FOR SEQ ID NO:48:

(i) SEQUENCE CHARACTERISTICS:
(A) LENGTH: 10 base pairs
(B) TYPE:nucleic acid
(C) STRANDEDNESS:single
(D) TOPOLOGY:linear (ii) MOLECULE TYPE:DNA (xi) SEQUENCE DESCRIPTION: SEQ ID NO:48:

GTGGGCGGGG 10

(2) INFORMATION FOR SEQ ID NO:49:

(i) SEQUENCE CHARACTERISTICS:
(A) LENGTH: 10 base pairs
(B) TYPE:nucleic acid
(C) STRANDEDNESS:single
(D) TOPOLOGY:linear (ii) MOLECULE TYPE:DNA ( x i ) SEQUENCE DESCRIPTION: SEQ ID NO:49:

GTGGGGGCTC                                                                                                                   10

( 2 ) INFORMATION FOR SEQ ID NO:50:

( i ) SEQUENCE CHARACTERISTICS:
        ( A ) LENGTH: 16 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:50:

TGTCGTGGGT GGATCC                                                                                                            16

( 2 ) INFORMATION FOR SEQ ID NO:51:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:51:

RTGGGBGGRY                                                                                                                   10

( 2 ) INFORMATION FOR SEQ ID NO:52:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:52:

AATTGTAAGC                                                                                                                   10

( 2 ) INFORMATION FOR SEQ ID NO:53:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:53:

TTAGGTAAAT                                                                                                                   10

( 2 ) INFORMATION FOR SEQ ID NO:54:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:54:

CGCTGTAATA                                                                                                                   10

-continued ( 2 ) INFORMATION FOR SEQ ID NO:55:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:55:

CCGTAAAGGG          10

( 2 ) INFORMATION FOR SEQ ID NO:56:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:56:

GCCTATAACG          10

( 2 ) INFORMATION FOR SEQ ID NO:57:

( i ) SEQUENCE CHARACTERISTICS:
        ( A ) LENGTH: 11 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:57:

GGGATAAACG C          11

( 2 ) INFORMATION FOR SEQ ID NO:58:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:58:

CATCTAACC          9

( 2 ) INFORMATION FOR SEQ ID NO:59:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:59:

CATCATAACC          10

( 2 ) INFORMATION FOR SEQ ID NO:60:

( i ) SEQUENCE CHARACTERISTICS:
        ( A ) LENGTH: 8 base pairs
        ( B ) TYPE:nucleic acid ( C ) STRANDEDNESS:single
( D ) TOPOLOGY:linear ( i i ) MOLECULE TYPE:DNA ( x i ) SEQUENCE DESCRIPTION: SEQ ID NO:60:

Y K R T A A M S    8

( 2 ) INFORMATION FOR SEQ ID NO:61:

( i ) SEQUENCE CHARACTERISTICS:
        ( A ) LENGTH: 10 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:61:

A A C C G G A A G T    10

( 2 ) INFORMATION FOR SEQ ID NO:62:

( i ) SEQUENCE CHARACTERISTICS:
        ( A ) LENGTH: 12 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:62:

C G T A C C G G A A  G G    12

( 2 ) INFORMATION FOR SEQ ID NO:63:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:63:

T C C G G A A G C    9

( 2 ) INFORMATION FOR SEQ ID NO:64:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:64:

T C C G G A A G C    9

( 2 ) INFORMATION FOR SEQ ID NO:65:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:65:

ACCGGAAGT 9

( 2 ) INFORMATION FOR SEQ ID NO:66:

( i ) SEQUENCE CHARACTERISTICS:
        ( A ) LENGTH: 9 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:66:

WCCGGAAGY 9

Having thus described our invention and the manner and process of making and using it in such full, clear, concise and exact terms so as to enable any person skilled in the art to which it pertains, or with which it is most nearly connected, to make and use the same;

We claim:

1. A method for simultaneously determining nucleotide recognition sequences for DNA-binding proteins, comprising:

(a) mixing (i) a set of oligonucleotide duplexes comprising 5' and 3' sequences that will hybridize to primers for amplification and an internal sequence of random nucleotides, (ii) an inhibitor of non-sequence specific binding of DNA-binding proteins to the oligonucleotide duplexes, and (iii) a cellular extract or nuclear extract containing DNA-binding proteins under conditions in which the concentration of oligonucleotide duplexes is at or below the average Kd value for specific binding between the oligonucleotide duplexes and the DNA-binding proteins;

(b) separating unbound oligonucleotide duplexes from oligonucleotide duplexes complexed with the DNA-binding proteins on the basis of differences in molecular weight;

(c) amplifying complexed duplexes to form amplified duplexes; and (d) analyzing the amplified duplexes to determine nucleotide recognition sequences for the DNA-binding proteins.

2. A method for simultaneously isolating nucleotide recognition sequences for DNA-binding proteins, comprising:

(a) mixing (i) a set of oligonucleotide duplexes comprising 5' and 3' sequences that will hybridize to primers for amplification and an internal sequence of random nucleotides, (ii) an inhibitor of non-sequence specific binding of DNA-binding proteins to the oligonucleotide duplexes, and (iii) a cellular extract or nuclear extract containing DNA-binding proteins under conditions in which the concentration of oligonucleotide duplexes is at or below the average Kd value for specific binding between the oligonucleotide duplexes and the DNA-binding proteins;

(b) separating unbound oligonucleotide duplexes from oligonucleotide duplexes complexed with the DNA-binding proteins on the basis of differences in molecular weight;

(c) amplifying complexed duplexes to form amplified duplexes;

thereby isolating nucleotide recognition sequences for DNA-binding proteins.

3. The method of either of claims 1 or 2, further comprising, subsequent to step (c):

(c)(1) mixing the amplified duplexes with the cellular extract or nuclear extract containing DNA-binding proteins;

(c)(2) separating unbound amplified duplexes from amplified duplexes complexed with the DNA-binding proteins on the basis of differences in molecular weight; and (c)(3) amplifying the complexed duplexes from step (c)(2) to form amplified duplexes;

wherein steps (c)(1) through (c)(3) are performed one or more times.

4. The method of claim 3, wherein the steps (c)(1) through (c)(3) are performed three times.

5. The method of either of claims 1 or 2, wherein the 5' and 3' sequences each have a restriction site.

6. The method of either of claims 1 or 2, wherein the internal sequence is from about 6 to about 25 base pairs.

7. The method of either of claims 1 or 2, wherein the non-specific inhibitor is poly(dI-dC).

8. The method of either of claims 1 or 2, wherein the separating step uses polyacrylamide gel electrophoresis.

9. The method of claim 1, wherein the analyzing step comprises:

(d)(1) ligating the amplified duplexes to a vector to generate clones; and (d)(2) determining the DNA sequences of the cloned duplexes.

10. The method of either of claims 1 or 2, wherein the oligonucleotide duplexes are labeled.

* * * * *